United States Patent
Chiang

[11] Patent Number: 5,867,841
[45] Date of Patent: Feb. 9, 1999

[54] VENTILATED SPORT GOGGLE STRUCTURE

[76] Inventor: Herman Chiang, 11F, No. 634-9, Ching-Ping Rd, Chung-Ho City, Taipei, Taiwan

[21] Appl. No.: 921,740

[22] Filed: Aug. 27, 1997

[51] Int. Cl.⁶ .................................................. A61F 9/02
[52] U.S. Cl. ................................................. 2/436; 2/439
[58] Field of Search ................................ 2/435, 436, 437, 2/445, 439, 428, 446, 426, 440, 431

[56] References Cited

U.S. PATENT DOCUMENTS

| | | | |
|---|---|---|---|
| 1,306,357 | 6/1919 | Shindel | 2/425 |
| 2,388,205 | 10/1945 | Bernheim et al. | 2/452 |
| 2,708,224 | 1/1955 | Lindblom | 2/428 |
| 3,368,221 | 2/1968 | Anderson | 2/425 |
| 4,087,865 | 5/1978 | Garofalo | 2/428 |
| 5,027,443 | 7/1991 | Watkins | 2/437 |
| 5,245,709 | 9/1993 | Shipcott | 2/425 |

Primary Examiner—Michael A. Neas
Assistant Examiner—Larry D. Worrell, Jr.
Attorney, Agent, or Firm—Pro-Techtor International Services

[57] ABSTRACT

A sport goggle structure includes a rim having an inner circumference along which a circumferential slot is formed to receive and hold therein a lens and a head strap having two ends respectively connected to connecting holes formed on two opposite lateral side edges of the rim. The circumferential slot of the rim has a minimum depth that is sufficient to receive a circumferential edge of the lens in order to minimize the size of the rim. The size-minimized rim has ventilation device and face contact device provided thereon. The face contact device is to provide a more comfortable and position-secured engagement with wearer's face. The ventilation device is to guide fresh air flow from outside goggles through a right-angled bend and directly toward an inner surface of the lens to provide the best defogging effect.

6 Claims, 8 Drawing Sheets

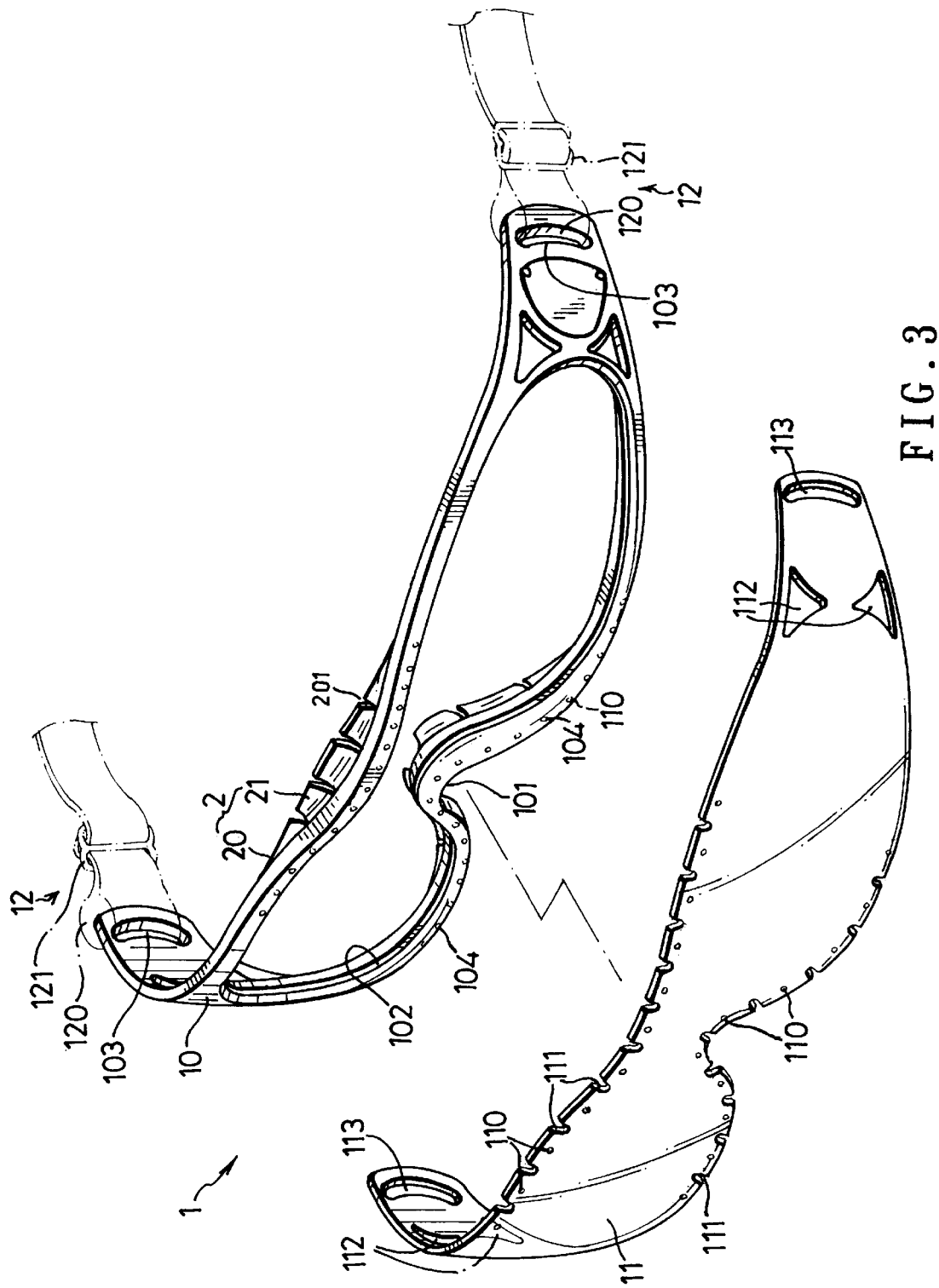

VENTILATED SPORT GOGGLE STRUCTURE

FIELD OF THE INVENTION

The present invention relates generally to sport goggles and in particular to the sport goggles that have a better positioning capability and improved ventilation and heat removal for defogging purpose.

BACKGROUND OF THE INVENTION

Sport goggles are used to protect the athletes from being damaged by particles or dusts carried in the air during doing exercise or playing a game. Generally speaking, when a person is doing violent activities, heat is generated by one's body and is removed by being dissipated through one's skin. The heat that is dissipated through the face of the wearer of the sport goggles may cause fog on the lens of the goggles. This affects the vision of the wearer. Further, without suitable ventilation between inside and outside of the goggles, the wearer's eyes may feel uncomfortable with no fresh air supplied thereto. Thus ventilation to supply fresh air and to defog is an important factor of the design of sport goggles.

Conventionally, the ventilation means is either provided on the rim of the goggles or on the lens of the goggles. In the former case, the rim has to be widened to accommodate the ventilation holes. This makes the goggles very bulky. Further, the widened rim increases the distance between the lens and the wearer's eyes and thus may cause unwanted limitation on the wearer's vision. For the ventilation means that is mounted on the lens, to avoid interference with wearer's vision, the lens is usually enlarged and such a large lens is, of course, more costly.

In FIG. 1 of the attached drawings, a conventionally sport goggle structure indicated at 5 is shown which is particularly suitable for horse racing. The goggles 5 comprise a rim 50, a lens 51 and a head strap 52. The rim 50 has an inner circumference along which a circumferential slot 501 is formed for receiving and holding therein the lens 51. Retainer members 502 are provided in the slot 501, preferably at positions corresponding to the upper and lower side of the bridge of the goggles 5, to engage notches 511 formed on the lens 51 for retaining the lens 51 on the rim 50. Openings 503 are provided on two opposite sides of the rim 50 for connection with the head strap 52.

The conventional sport goggles 5, however, have disadvantages and one of the disadvantages is that the goggles 5 are ready to move relative to the wearer's face when the wearer's facial muscle moves or acts. With reference to FIGS. 2A and 2B for further explanation of the relative movement of the conventional goggles 5 with respect to the wearer's face, generally speaking, in the human head skeleton, a recessed portion is present between the eyebrows and the face contour is different from person to person so that the conventional goggles 5 that are worn to cover the area around the eyes are not capable to completely comply with the face contour of the wearer, especially at the recessed portion between the eyebrows and a gap is present between the upper edge of the rim 50 and the recessed portion of the face contour 60 as indicated in FIG. 2A. Thus, facial muscle movements, such as frowning, may cause the goggles to move upward relative to the face (see dashed line in FIG. 2B) and repeated muscle movements will finally move the goggles 5 to such a position that is uncomfortable to the wearer.

Thus it is desirable to provide a sport goggle structure which provides a better compliance with and a more close engagement with the wearer's face contour and thus reduces and even eliminates the movement of the goggles relative to the wearer's face caused by facial muscle movement.

SUMMARY OF THE INVENTION

An object of the present invention is to provide a sport goggle structure which is constructed to more closely comply with the wearer's face contour so as to reduce or eliminate the relative movement of the goggles with respect to the wearer's face.

Another object of the present invention is to provide a sport goggle structure which has an improved ventilation structure so as to more effectively maintain the lens clear by defogging with fresh air flow and supply fresh air to the wearer's eyes.

A further object of the present invention is to provide a sport goggle structure which not only protects the wearer's eyes from damage by particles or dusts carried in the air, but is also comfortable in wearing and fashionable in style.

To achieve the above objects, in accordance with the present invention, there is provided a sport goggle structure, comprising a rim having an inner circumference along which a circumferential slot is formed for receiving a circumferential edge of a lens and thus holding the lens on the rim and a head strap having two ends respectively connected to two opposite lateral side edges of the rim. The slot has a minimum depth that is just sufficient to receive and hold the edge of the lens therein in order to minimize the size of the rim. The rim comprises a plurality of ventilation air passages therein with inlet opening on the outward facing side and outlet opening on the facing wearer side so as to guide fresh air flows into the inner side of the goggles. The air passages are bent so as to conduct the air flow directly toward the inner surface of the lens to provide a better defogging effect.

In accordance with another aspect of the present invention, the goggle rim comprises at least one face contact device on the upper edge of the rim, which face contact device is generally soft and flexible to provide a better compliance with the wearer's face contour for more securely holding the goggles in position on the wearer's face. In accordance with the present invention, the face contact device comprises a plurality of base sections integrally extending from the rim, each having a contact section extending therefrom to define a free end for comfortable contact engagement with the wearer's face. Slits are provided to separate the base sections, as well as the contact sections thereof, from each other for a greater flexibility thereof to more closely contact and comply with the face contour, especially the recessed portion between the eyebrows.

In accordance with the present invention, a second face contact device may be optionally provided on the lower edge of the rim at the position corresponding to the wearer's nose so as to provide a more comfortable engagement between the goggles and the wearer's nose.

The objects, advantages and features of the present invention will be apparent from the following description of preferred embodiments thereof, with reference to the attached drawings, wherein:

BRIEF DESCRIPTION OF THE DRAWINGS

FIG. 3 is an exploded perspective view showing a sport goggle structure in accordance with the present invention;

DETAILED DESCRIPTION OF THE PREFERRED EMBODIMENTS

Figure 6:
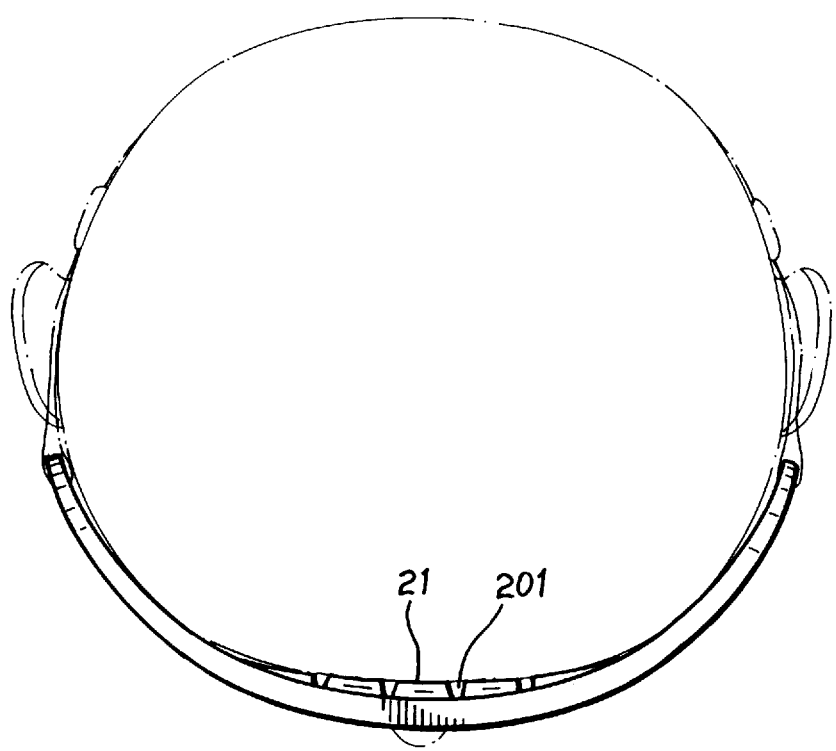
FIG. 6 is a top view showing a wearer wearing the sport goggles in accordance with the present invention.

Referring to the drawings and in particular to FIG. 3, wherein a sport goggle structure in accordance with the present invention, generally designated with reference numeral 1, is shown, the sport goggles 1 comprise a rim 10, a lens 11, a head strap 12 and face contact means 2. The rim 10 is made by means of for example injection molding to form a hollow frame like structure, having an upper edge, an opposite lower edge connected to each other by two lateral edges, a recess 101 being formed on middle of the lower edge thereof to straddle over wearer's nose (not shown). The rim 10 has an inner circumference along which a circumferential slot 102 is formed to receive a circumferential edge of the lens 11 for holding the lens 11 therein. The slot 102 may has a minimum depth which is sufficient to receive and hold the edge of the lens 11 so as to reduce the size and weight of the rim 10. On each of two opposite lateral edges of the rim 10, a connection hole 103 is provided for connecting an end of the head strap 12. The face contact means 2 is provided along a central portion of the upper edge of the rim 10, which comprises a plurality of base sections 20 integrally formed with and extending from the rim 10, each having a contact section 21 extending therefrom to define free ends which define a curve corresponding to the wearer's face skeleton for compliant contact engagement with a wearer's face (see FIG. 6). Also referring to FIG. 4B, the base sections 20 extend a distance from the rim 10 with the contact sections 21 further extending therefrom in an upward inclined manner for more comfortable engagement with the wearer's face. The contact sections 21 have a largest size at the middle of the top edge of the rim 10 and gradually reduced toward the two lateral side edges of the rim 10 to finally coincident therewith. The contact sections 21 have a thickness reduced from the base sections 20 to a minimum at the free ends thereof for providing a better and more comfortable contact with the wearer's face. The face contact means 2 comprises a plurality of slits 201 extending from the free ends of the contact sections 21 to the base sections 20 for separating the adjacent ones of the base sections 20 as well as the contact sections 21 so as to provide the face contact means 2 with a better compliance with the wearer's face contour. Thus, the goggles 1 may closely and compliantly contact the face contour of the wearer, even at the recessed portion between the eyebrows, as shown in FIG. 6.

Figure 5:
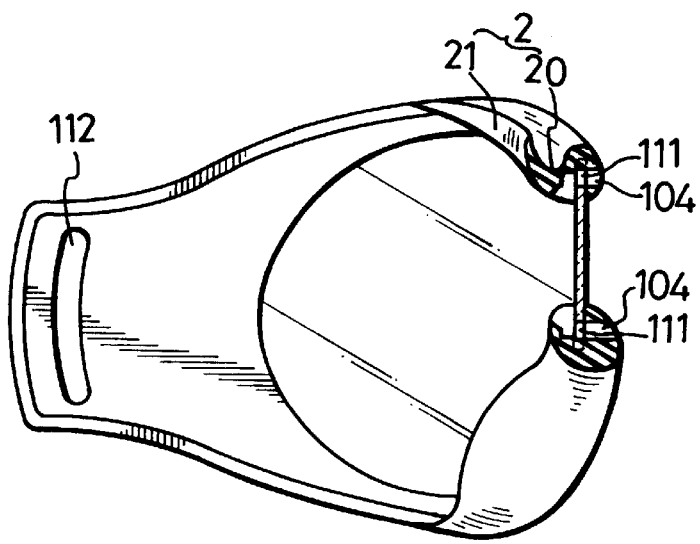
FIG. 5 is a side elevational view, partially broken, of the sport goggles of the present invention.

The rim 10 comprises a plurality of ventilation passages 104 arranged along the central portions of the upper edge and the lower edge thereof, each having an inlet opening, preferably a circular opening, on an outward facing side of the rim 10 and an outlet opening on a facing wearer side of the rim 10 and arranged to be located in the proximity of the lens 10 so as to allow fresh air to flow therethrough from outside the goggles 1 to the inside thereof, as shown in FIG. 5 and guided directly toward an inner surface of the lens 10. Each of the air passages 104 have a substantially right angle bend so that the inlet opening thereof has a central axis that is substantially normal to that of the outlet opening. Preferably, the outlet opening has a size greater than that of the inlet opening so as to define a diverging configuration of the air passage 104 at the outlet thereof Thus, fresh air of the atmosphere which is guided by the bent passages 104 formed in the rim 10 and extending from the inlet openings of the passages 104 directly toward the inside surface of the lens 11 provide an effective defogging operation on the lens 11.

The lens 11 has a shape and size corresponding to the rim 10 to be received within the circumferential slot 102 of the rim 10. Preferably, the lens 11 has a plurality of apertures 110 formed thereon which allows the lens 11 to be integrally secured to the rim 10 in the injection molding process of the rim 10 by having the molding material flowing through and partially staying in the apertures 110. Once the molding material cures, the lens 11 is securely and integrally mounted to the rim 10. The lens 11 also comprises a plurality of openings 111 which are preferably located between two adjacent ones of the apertures 110. The openings 111 are corresponding to the air passages 104 of the rim 10 so as not to block air flow through the air passages 104 into the inner side of the goggles 1, as shown in FIG. 5.

The lens 11 also comprises mounting holes 112 at each of two opposite lateral sides thereof which allow the lens 11 to be more securely fixed to the rim 10 and also provide decoration purpose. An elongated slot 113 is provided on the lens 11 to be adjacent to the mounting holes 112 and in alignment with the connection holes 103 of the rim 10 for receiving the insertion of the head strap 12. The head strap 12 which comprises two end portions respectively connected to the rim 10 by being secured to both the connection holes 103 of the rim 10 and the slots 113 of the lens 10 comprises a stretchable member 120 constituting each of the end portions thereof on which a strap length adjusting member 121 is mounted.

Figure 1:
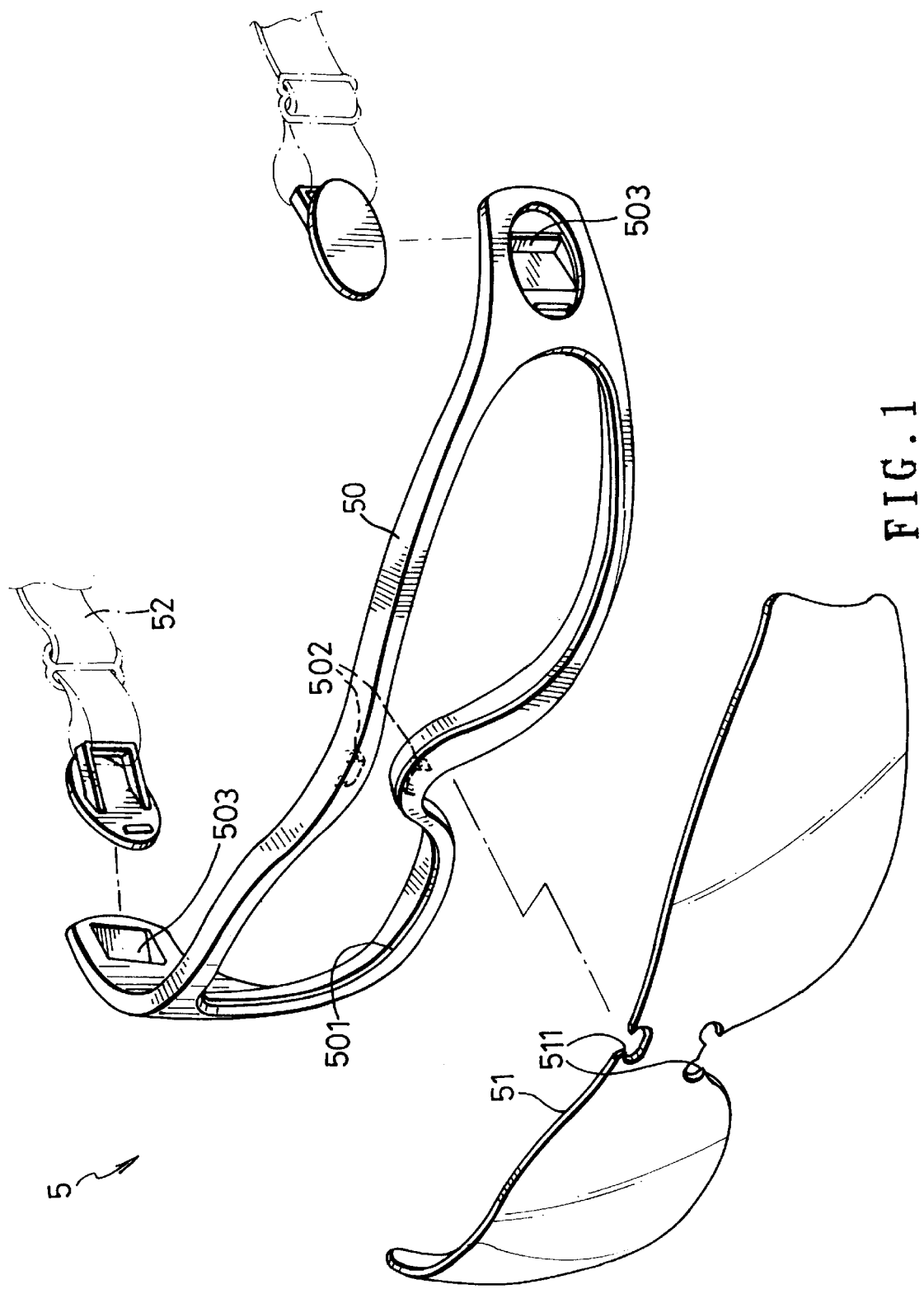
FIG. 1 is an exploded perspective view showing a conventional sport goggle structure.
Figure 2:
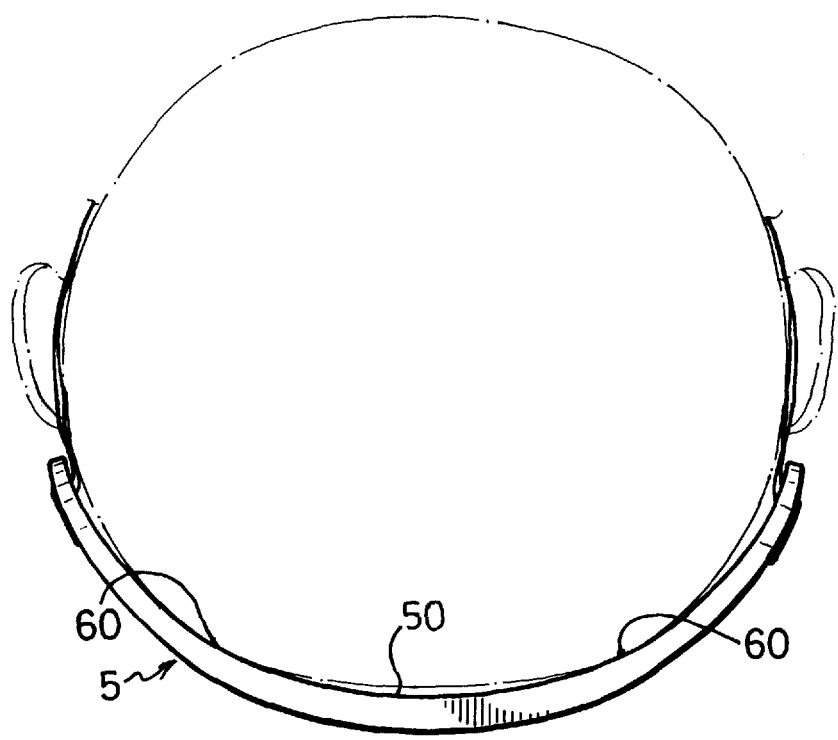
FIG. 2A is a top view showing a wearer wearing the conventional goggles.
FIG. 2B is a front view showing the wearer wearing the conventional goggles.
Figure 2:
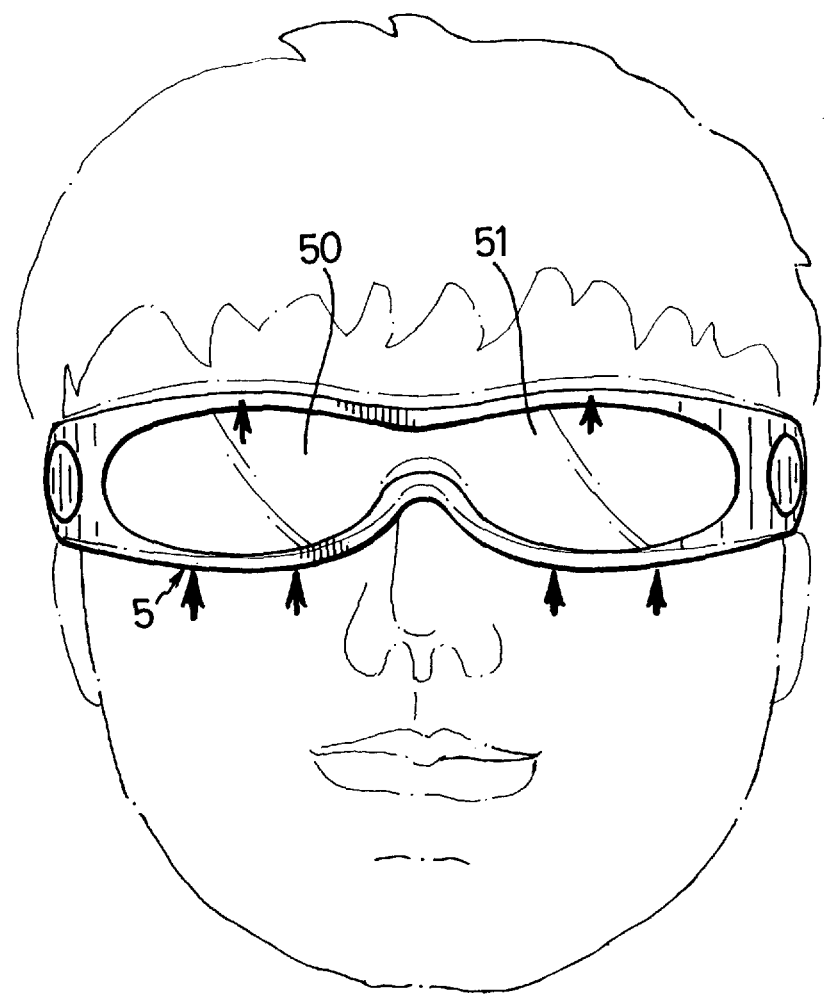
Figure 4A:
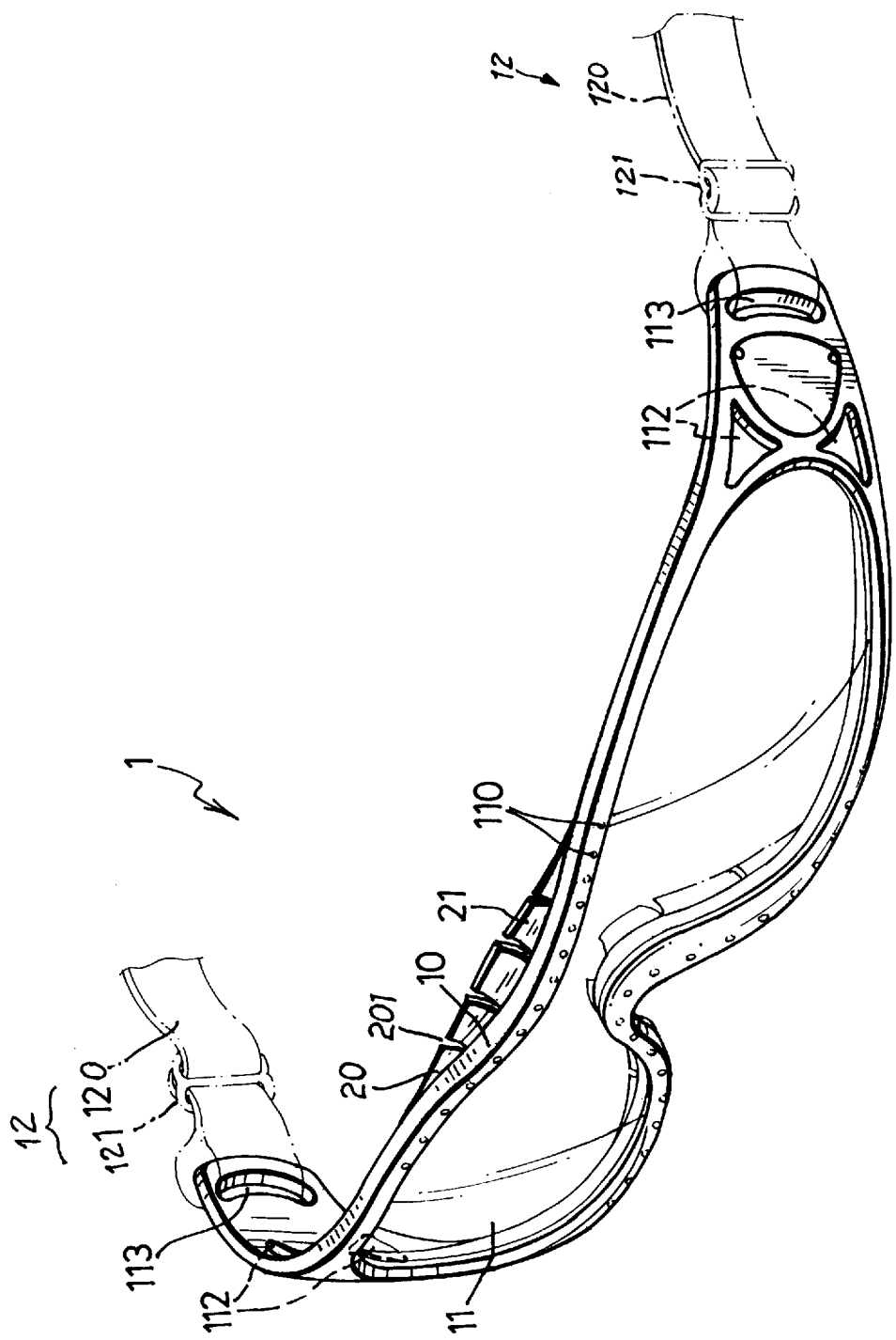
FIG. 4A is a perspective view showing the sport goggles of the present invention.
Figure 4:
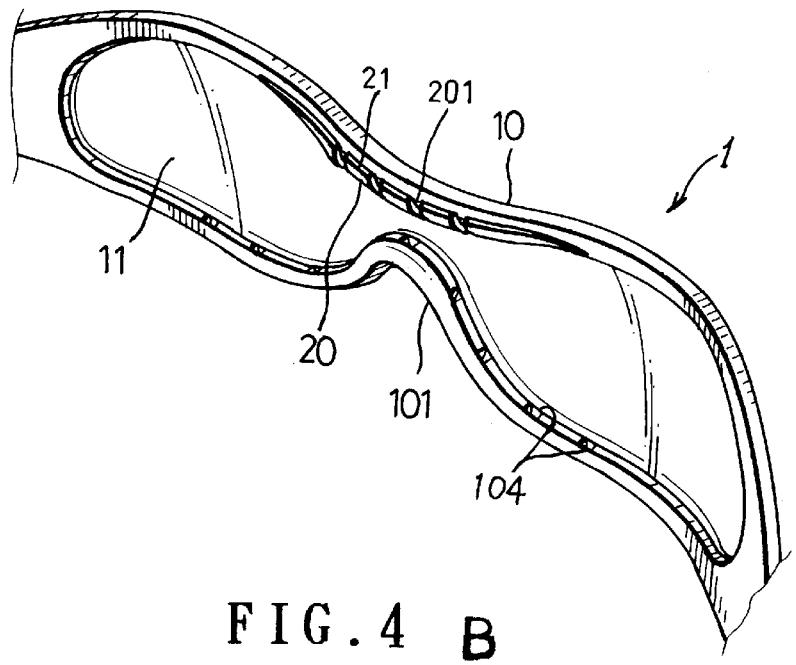
FIG. 4B is a perspective view showing a portion of the sport goggles of the present invention viewed from the facing wearer side.

A fully assembled condition of the goggles 1 is illustrated in FIG. 4A wherein the contact sections 21 of the face contact means 2 provide an improved, more position-secured and more comfortable contact engagement with the wearer's face. As shown in FIG. 6, in wearing the goggles 1 of the present invention, the improved face contour compliance provided by the slits 201 of the face contact means 2 and the flexibility of the material that makes the face contact means 2 allows the goggles 1 to be more securely positioned on the wearer's face with an improved face contour compliance with the wearer's face. Thus the movement of the facial muscles of the wearer, such as frowning, will not move the goggles 1 with respect to the wearer's face.

Figure 7:
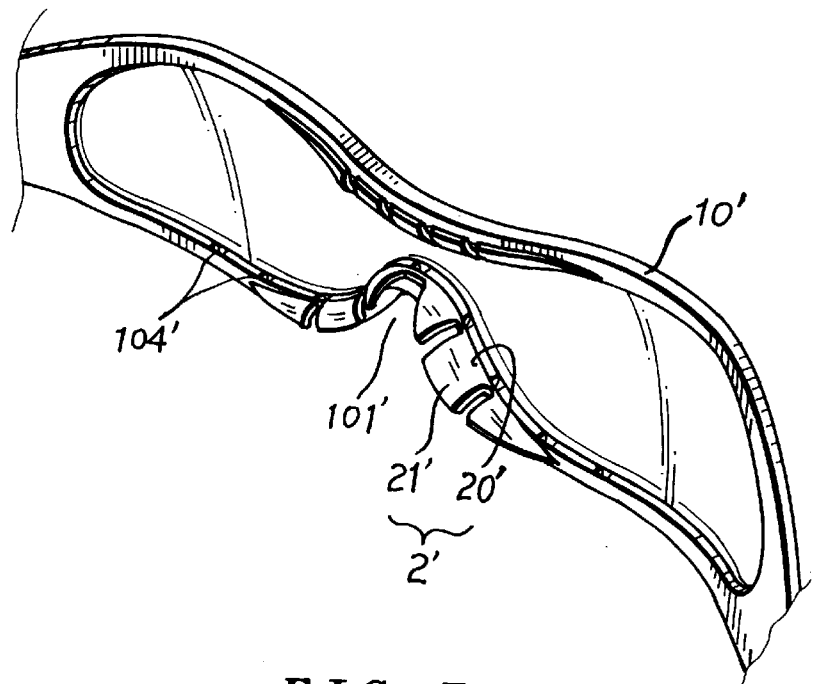
FIG. 7 is a perspective view showing a portion of a sport goggle structure in accordance with a second embodiment of the present invention.
Figure 8:
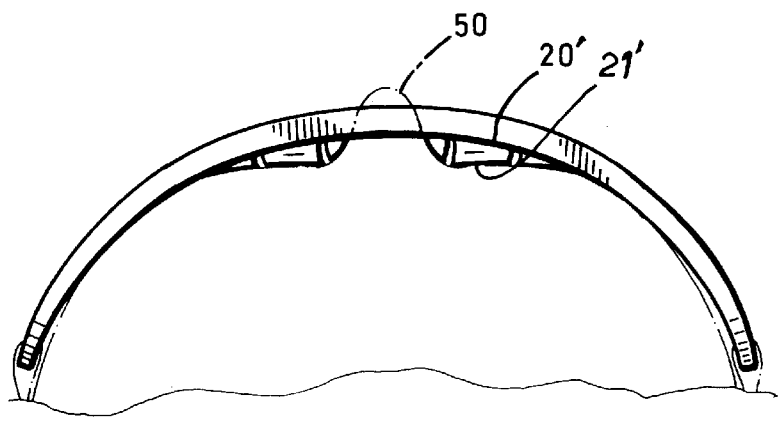
FIG. 8 is a bottom view showing a wearer wearing the second embodiment sport goggles of the present invention.

In the above description, the face contact means 2 is only provided along the central portion of the upper edge of the rim 10. If desired, a similar structure may be provided on the lower edge of the rim 10. In a second embodiment of the present invention illustrated in FIG. 7, the rim is provided with face contact means on both the upper edge and the lower edge thereof. In accordance with the second embodiment, the rim which is now designated at 10' for distinction from the first embodiment and having a nose recess 101' at the middle of the lower edge thereof comprises second face contact means 2' on the lower edge. The second face contact means 2' comprises a plurality of base sections 20' integrally formed with and extending from the lower edge of the rim 10' and located at both sides of the nose recess 101'. Each of the base sections 20' has a contact section 21' extending therefrom to define a free end for contact engagement with the wearer's face. The base sections 20' are arranged to extend a distance away from the lower edge of the rim 10' with the contact section 21' further extending therefrom in a downward inclined manner to provide a better compliance with the wearer's face. Each of the contact sections 21' has a thickness reduced from the base section 20' toward the free end thereof for more comfortable contact engagement with the wearer's nose, as shown in FIG. 8. A plurality of air passages 104' are provided in the rim 10' as discussed in the first embodiment. The second face contact means 2' on the lower edge of the rim 10', together with the first contact means on the upper edge of the rim 10', provides the goggles of the present invention with the capability of precisely positioning and more securely holding the goggles 1 on the wearer's face. The air passages 104' provide an effective removal of heat generated by the wearer's face during exercise so as to keep the lens clear.

The above description is made with respect to the preferred embodiments of the present invention and for those skilled in the art, it is possible to make a variety of modifications and changes to the above-described specific embodiments without departing from the scope and spirit of the present invention. All these modifications and changes should be considered within the scope of the present invention as defined in the appended claims.

What is claimed is:

1. A sport goggle structure, comprising:

a rim, having an inner circumference along which a circumferential slot is formed and connecting holes on two opposite lateral edges thereof, a lens having a circumferential edge received within the circumferential slot of the rim, ventilation means provided on the rim, comprising a plurality of inlet openings formed on an outward facing side, each inlet opening having an air passage extending therefrom to define an outlet opening on the side facing the wearer and configured to guide air flow directly toward an inner surface of the lens, each of the inlet openings of the ventilation means has a central axis and the outlet opening thereof has a central axis substantially normal to the central axis of the inlet opening, the outlet openings are located in the proximity of the lens, the inlet openings of the ventilation means have a circular shape, and the outlet openings have a size greater than the associated inlet openings so as to define a diverging section of the associated air passage, and a head strap having two ends respectively secured to the connecting holes on the two lateral edges of the rim, the rim comprises face contact means on an upper edge thereof to provide a compliant contact engagement with a wearer's face, the face contact means comprises a plurality of base sections which are integrally formed with and extend toward the wearer from a central portion of the rim that corresponds to a portion of the wearer's face between the wearer's eyebrows, each of the base sections having a contact section which extends from the base section, each of the base sections extending from the rim to a predetermined distance from which the contact means further extends to define a curve that conforms to the wearer's face contour.

2. The sport goggle structure as claimed in claim 1, wherein the face contact means comprises slits extending at least through the contact sections to separate the contact sections from each other.

3. The sport goggle structure as claimed in claim 2, wherein the slits further extend through the base sections to reach the rim so as to divide the face contact means into separate sections.

4. The sport goggle structure as claimed in claim 9, wherein the rim has a lower edge on which a recess is formed for accommodating the wearer's nose, second face contact means being provided on two sides of the recess, which second face contact means has a structure similar to the face contact means that is provided on the upper edge of the rim.

5. A sport goggle structure, comprising a rim made by means of molding, having an inner circumference along which a circumferential slot is formed and connecting holes on two opposite lateral edges thereof, a recess being provided on a lower edge of the rim, a lens having a circumferential edge received within the circumferential slot of the rim and a head strap having two ends respectively secured to the connecting holes on the two lateral edges of the rim, the lens comprising a plurality of apertures arranged along the circumferential edge of the lens which allows molding material to flow therethrough and cured therein during molding operation so as to integrally mount the lens to the rim, the lens also comprising a plurality of openings, the rim comprising ventilation means provided thereon, the ventilation means comprising a plurality of inlet openings formed on an outward facing side, each inlet opening having an air passage extending therefrom through the rim to define an outlet opening on the side of the rim facing the wearer, each of the inlet openings of the ventilation means is circular and has a central axis and the outlet opening thereof has a central axis substantially normal to the central axis of the inlet opening, the outlet openings are located in the proximity of the lens, the outlet openings have a size greater than the associated inlet openings so as to define a diverging section of the associated air passage; and the rim comprises first face contact means on an upper edge thereof to be located between eyebrows of a wearer and second face contact means on a lower edge thereof to be located on two sides of nose of the wearer for providing a compliant contact engagement with face of the wearer, the face contact means comprises a plurality of base sections which are integrally formed with and extending toward the wearer from a portion of the rim, each of the base sections having a contact section extending therefrom, each of the base sections extending from the rim to a predetermined distance from which the contact means further extends to define a curve that is fit for the wearer's face contour, the face contact means comprises slits extending at least through the contact sections to separate the contact sections from each other.

6. A sport goggle structure, comprising a rim made by means of molding, having an inner circumference along which a circumferential slot is formed and connecting holes formed on two opposite lateral edges thereof, a lens having a circumferential edge received within the circumferential slot of the rim and a head strap having two ends respectively secured to the connecting holes on the two lateral edges of the rim, the lens comprising a plurality of apertures along the circumferential edge thereof which allows molding material to flow therethrough and to be cured therein during a molding operation so as to integrally mount the lens to the rim, the rim comprises face contact means provided on at least an upper edge of the rim, the face contact means comprises a plurality of base sections which are integrally formed with and extending toward the wearer from a portion of the rim, each of the base sections having a contact section extending therefrom, each of the base sections extending from the rim to a predetermined distance from which the contact means further extends to define a curve that is fit for the wearer's face contour, the face contact means comprises slits extending at least through the contact sections to separate the contact sections from each other.

* * * * *